(12) United States Patent
Wohlgemuth et al.

(10) Patent No.: US 8,948,472 B2
(45) Date of Patent: Feb. 3, 2015

(54) AUTOMATED IMAGING DEVICE AND METHOD FOR REGISTRATION OF ANATOMICAL STRUCTURES

(75) Inventors: Richard Wohlgemuth, Bad Tölz (DE); Gregor Tuma, Munich (DE)

(73) Assignee: Brainlab AG, Feldkirchen (DE)

( * ) Notice: Subject to any disclaimer, the term of this patent is extended or adjusted under 35 U.S.C. 154(b) by 2144 days.

(21) Appl. No.: 12/017,820

(22) Filed: Jan. 22, 2008

(65) Prior Publication Data

US 2009/0046906 A1 Feb. 19, 2009

Related U.S. Application Data

(60) Provisional application No. 60/887,976, filed on Feb. 2, 2007.

(30) Foreign Application Priority Data

Jan. 22, 2007 (EP) .................................. 07001290

(51) Int. Cl.
*G06K 9/00* (2006.01)
*A61B 6/00* (2006.01)
*A61B 19/00* (2006.01)

(52) U.S. Cl.
CPC ............ *A61B 6/488* (2013.01); *A61B 6/4476* (2013.01); *A61B 6/469* (2013.01); *A61B 6/547* (2013.01); *A61B 19/52* (2013.01); *A61B 19/5244* (2013.01); *A61B 19/50* (2013.01); *A61B 2019/501* (2013.01); *A61B 2019/505* (2013.01); *A61B 2019/5255* (2013.01); *A61B 2019/566* (2013.01); *Y10S 128/92* (2013.01); *Y10S 128/922* (2013.01); *Y10S 128/923* (2013.01)
USPC ........... 382/128; 382/130; 382/131; 382/132; 128/920; 128/922; 128/923

(58) Field of Classification Search
USPC ............ 382/128, 130, 131, 132; 378/4, 8, 20, 378/21; 600/407, 410; 128/920, 922
See application file for complete search history.

(56) References Cited

U.S. PATENT DOCUMENTS

| | | | |
|---|---|---|---|
| 6,195,409 B1 | 2/2001 | Chang et al. | |
| 6,415,048 B1 * | 7/2002 | Schneider | 382/131 |
| 2005/0010106 A1 * | 1/2005 | Lang et al. | 600/425 |
| 2005/0147283 A1 * | 7/2005 | Dwyer et al. | 382/128 |
| 2005/0192495 A1 | 9/2005 | Makram-Ebeid et al. | |
| 2007/0071168 A1 * | 3/2007 | Allison et al. | 378/65 |
| 2007/0127790 A1 * | 6/2007 | Lau et al. | 382/128 |

FOREIGN PATENT DOCUMENTS

EP 1 693 798 A1 8/2006

* cited by examiner

*Primary Examiner* — Nicole Ippolito
(74) *Attorney, Agent, or Firm* — Tucker Ellis LLP

(57) ABSTRACT

A device and method for capturing images of a specific part of an anatomical structure using a series of images, wherein an image is taken of the anatomical structure and is compared to a database of information is order to determine and optimize the imaging conditions used for taken subsequent images of the specific part.

22 Claims, 3 Drawing Sheets

AUTOMATED IMAGING DEVICE AND METHOD FOR REGISTRATION OF ANATOMICAL STRUCTURES

RELATED APPLICATION DATA

This application claims priority from Provisional Ser. No. 60/887,976, filed Feb. 2, 2007, and EP 07 001 290.1, filed Jan. 22, 2007, which are incorporated by reference.

FIELD OF THE INVENTION

The present invention relates to methods and devices for capturing a specific part of an anatomical structure of a human or animal by taking a series of images.

BACKGROUND OF THE INVENTION

In past medical treatment practice, when images are taken of a patient, the patient may be lying on a couch and an imaging apparatus such as an x-ray machine may be next to the patient. This x-ray machine may be positioned at a determined location relative to the couch and may be used to image a specific part of the anatomical structure of the patient, for example the pelvis. Often, the specific part is not captured by the first image. The physician then corrects the location of the x-ray machine and takes a second image. If the second image again does not capture the specific part, then yet another image may be necessary.

SUMMARY OF THE INVENTION

Often the physician is concerned with a specific part of a patient's anatomy. The devices and methods in accordance with the invention provide a way to optimize the imaging of that specific part and they are described in detail below.

A part of an anatomical structure may be imaged by an imaging apparatus.

This part is called an "imaged part" and the image is called a "first image." The imaged part can correspond to a "specific part," i.e., a part of interest to the physician. In the first image, however, this is often not the case. The first image may be taken under particular "imaging conditions" including the direction from which the image is taken (the "imaging direction"). When imaging, the imaging apparatus is capable of capturing a certain range. This range is called the "imaging range" and is another example of an imaging condition. The imaging range may be the space from which a set of imaging signals are detected by the imaging apparatus. This imaging range may be determined by many variables including: the imaging optics, the distance between the imaging apparatus and the imaged part, and/or by the type, shape, and size of the imaging sensor in the apparatus. Thus, the imaging conditions may include the imaging direction and/or imaging range.

Examples of imaging apparatus can include an x-ray machine such as a CT scanner; an MR scanner; and/or an ultrasound scanner. Therefore images can include x-ray recordings, nuclear spin recordings and ultrasound recordings.

The specific part of the anatomical structure can be characterized or identified by specific information. A database containing such information, including images of a number of specific parts, can be stored in a computer memory. The database can also contain general information concerning typical human anatomical structures and/or information specific to the patient to be examined. The database can also contain information concerning the imaged part and the specific part, and their relative locations. The relative location information can be related to a typical human anatomical structure or related to particular human variations such as sex, height, weight, age, and the like. The information can also include the relative locations of anatomical parts in a patient to be examined, and for whom the specific part is to be captured.

A query or search of the database allows at least some of the imaging conditions to be determined. By making a comparison with the data in the database concerning the anatomical structure, it is possible to ascertain the size of the captured section of the anatomical structure. From the relative location of landmarks or prominent lines, and the shape of the lines or outlines of bone structures, it is possible to identify the direction from which the image was taken. These landmarks and lines can be automatically extracted by pattern recognition algorithms and/or contrast enhancing methods, and compared with corresponding data in the database.

The particular imaging conditions can be displayed or stored, such that a physician can use this information to make decisions concerning changes to the imaging conditions. In particular, the physician can decide whether to use the first image and leave the imaging apparatus where it was when the first image was taken, or whether to perform subsequent imaging. In accordance with the invention, the imaging conditions (or at least some of them) are preferably changed in subsequent imaging, either automatically by a device and/or by a software program loaded and running on a device. The imaging conditions may be changed automatically, when an imaging comparison, e.g., a comparison between the image and the data stored in the database, determines that the imaged part does not correspond to the specific part. Preferably, a user may provide information concerning the specific part, which allows the specific part to be identified in the database. This information concerning the specific part may include details that allow the location of the specific part in the anatomical structure to be determined. This information may also include details which determine the size of the specific part to be captured. A user entering the term "pelvis," for example, may result in the determination of the location and size of that specific part in the anatomic structure.

The information may also include the desired imaging conditions, for example, the direction from which the specific part is to be imaged. In other words, the information may include information concerning the orientation of the specific part relative to the imaging apparatus. The imaging conditions determined may be compared with the information concerning the specific part, and the imaging conditions for subsequent imaging can be changed based on the information in the database, such that the specific part can be captured using the new imaging conditions. With the new imaging conditions, the specific part may be captured in the desired size and/or resolution, and/or from the appropriate orientation (i.e., from the correct imaging direction).

Information for locating the specific part in the database may be provided, such as terms that identify the specific part. For example, anatomical terms such as acetabulum, neck of the femur, etc., can be used. The extent or size of the specific part can also be specified. For example, the cervical vertebral column (CVC) can be specified from C1 to C7.

With the aid of the database, it is possible to determine the relative location and/or size of the specific part relative to the imaged part and also relative to the imaging range. If this relative location and/or size is known, then the imaging range can be changed using the imaging apparatus. The imaging apparatus can be moved, or the imaging optics can be changed in order to change the range at which it is sensitive to imaging. By making these changes to the imaging conditions, it is possible to set imaging range and imaging direction parameters for the next image recording that are appropriate for capturing the specific part. Thus, the specific part may be captured within the imaging range and recorded from a desired direction.

On the basis of relative location and/or determined size, the imaging conditions, or at least some of them, can be changed in order to capture the specific part in the next recording. In the embodiments herein, the term "relative location" can also include an orientation of the imaged part relative to the specific part (i.e., a relation between the recording direction of the imaged part and a desired recording direction for the specific part).

In addition to information identifying or describing the specific part, additional information can be provided such as: the type of imaging, a desired imaging condition, a desired recording direction, and/or a desired imaging range. Such information may be referred to as "type information." Examples could include a recording taken from a lateral direction or from 50° relative to the median sagittal plane. Another example of type information could be a diagnostic hypothesis to be clarified. Thus, for example, when the user enters "CVC trauma," the database could be automatically queried for imaging conditions ideal for clarifying this specific diagnostic hypothesis. In greater detail, if for example "CVC trauma" is entered, an image of C1 to C7 both from the front and laterally can be recorded, to assess a kyphosis of the CVC. Thus, by entering particular terms, a specific part of the anatomical structure can be automatically selected based on the type information, and particular imaging conditions and a minimum number of images may be automatically selected. For another example, if osteoporosis is suspected in the range L4/L5, different imaging conditions may be desirable than if a slipped disc is suspected in the range L4/L5. Thus, when changing the imaging conditions from image to image, the type information is helpful to produce the desired images.

If, after the imaging conditions have been changed—automatically—and the next image does not (desirably) capture the specific part, then the steps mentioned above may be repeated. In other words, the imaging conditions obtained or desired after the first image may again be obtained after a second or subsequent image, and may be automatically updated for another subsequent image (if desired) by using the information in the database. The repetition can be terminated once the specific part is captured in the images to a desired degree.

When comparing the imaged part with the data in the database, a preferred approach may be to assume that the imaged part is situated in the vicinity of the specific part. With this approach, the data processing and search process can be expedited.

The images taken may be two-dimensional images, wherein a three-dimensional model of the specific part can be produced from a series of two-dimensional images. In accordance with the invention, the series of two-dimensional images may be optimized in order to produce the three-dimensional model to the desired quality, using as few images as possible. In the example of x-ray images, minimizing the number of images can reduce the patient's exposure to harmful radiation.

The database may include different imaging conditions for different stored parts, each suitable for imaging the stored part. The database may be configured such that when three-dimensionally modelling one of the stored parts, particular imaging conditions are used to produce a three-dimensional model of the part of the anatomical structure that corresponds to the stored part. Preferably, the database may be queried to compare the known specific part with a stored part. The imaging conditions suitable for this stored part may then be recalled from the database, and the images may be taken in accordance with these stored imaging conditions. The imaging conditions may be changed from image to image, such that they correspond as far as possible to the stored imaging conditions, or in particular to the series of stored imaging conditions.

Alternatively or additionally in the case of three-dimensionally modelling of a specific part, the imaging conditions may be changed and a new image taken if a three-dimensional model of the specific part cannot be produced from the images obtained to date, or cannot be produced to the desired quality. The determination to take a new image can also be required if the calculation of the three-dimensional model of the specific part does not converge or does not meet predetermined criteria. In other words, if a sufficiently high level of accuracy or a sufficiently low error in the three-dimensional model cannot be produced, a new image is taken using imaging conditions that differ from those of the previous image. For example, the imaging direction might be changed. The imaging direction can be changed such that it deviates as far as possible from all the imaging directions used to date, to obtain additional information for modelling the three-dimensional model. A specific sequence of imaging conditions, such as imaging directions, can also be predetermined. The sequence may be discontinued once a three-dimensional model having the desired quality can be produced from the acquired images.

A learning algorithm may be used to optimize the changes to the imaging conditions and to learn from previous images used for modelling an earlier specific part. To this end, the imaging conditions used for imaging a specific part may be stored. The number of images that were necessary to produce the three-dimensional model having the desired quality may also be stored. In accordance with the learning algorithm, it may be possible to select, for future images, the imaging conditions that will lead to the desired result using the lowest number of images.

In accordance with another embodiment, in order to optimize the image sequences in the aforementioned process, the imaging conditions may be varied from image sequence to image sequence for a specific and/or stored part for producing a three-dimensional model. In this embodiment, the image sequence that produced the best quality and/or lowest number of images in producing a three-dimensional model may be selected.

When determining the imaging conditions, it is preferable to have information from which the location and/or orientation of the specific part relative to the recording apparatus can be deduced. A tracking device can be attached or secured to the patient, or if possible, directly to the anatomical structure. The tracking device may include marker elements, such as marker spheres, which have a predetermined spatial relation to each other and reflect or emit signals. The signals reflected or emitted by the markers may be detected by a sensor that can be part of a navigation system (for example an image-guided surgical system or IGS). On the basis of the detected signals, a data processing computer can then determine the location of the tracking device relative to the sensor and/or in a particular reference frame (for example, the space in which the examination is performed). If the tracking device is registered relative to an apparatus, anatomical structure, and/or a patient, then the location of the patient or anatomical structure can be determined. The tracking device can also be fastened to an orientation aid or a couch on which the patient is lying, or with respect to which the patient is oriented. By detecting the tracking device and assuming a typical posture for the patient, it is possible to deduce the location of the patient relative to the imaging apparatus. A tracking device can also be attached to the imaging apparatus itself, so as to deduce the relative location and orientation of the imaging apparatus relative to the patient, or relative to the specific part of the anatomical structure. Thus, by detecting the tracking device and evaluating the signals using a navigation system, when the relative location between the imaging apparatus and the tracking device is known, it is possible to deduce the imaging conditions.

In accordance with the invention, the imaging conditions can be determined without referring to information derived from the imaged part. The imaging conditions can also be used as a starting point and/or as additional information for determining the imaging conditions under which the imaged part was captured more quickly and effectively. The imaging conditions determined using the tracking device and the imaging conditions determined based on the image and the database, can be compared with each other and, if they deviate from each other, a weighted method can be used as the starting point for subsequent images and further changes to the imaging conditions.

Also provided herein is a software program that when loaded into a computer's memory and run, causes the computer to implement the method or methods disclosed herein, and to a corresponding computer program storage media that stores the program, or to a signal that transmits the program from one storage location to another (for example, downloading the program via the internet).

Also provided herein is a device that is designed to perform the method or methods in accordance with the invention. The device may include the imaging apparatus, such as x-ray, MRI, or ultrasound machine. The imaging apparatus may be designed to image a part of an anatomical structure. The images taken may be two-dimensional images and they may be taken under particular imaging conditions, as disclosed herein.

The device may also include a database in which information may be stored concerning the anatomical structure and/or particular parts of the anatomical structure, their characteristics, and/or their anatomical details. The device may also include a data processing computer that may perform determination and/or calculation steps. The data processing computer may be designed to query the database based on the image(s) taken by the imaging apparatus, i.e. based on the captured, imaged part. The data concerning the image(s) may be transferred from the imaging apparatus to the data processing computer. The data processing computer may also determine at least some of the imaging conditions, using the information stored in the database.

The device in accordance with the invention may also include an input device such as a keyboard, removable memory or user interface, that allows information concerning the specific part to be entered. Such information may include information that allows the specific part to be identified and/or determined in the database. The data processing computer may also determine, based on the determined imaging conditions, changes to be made to the imaging conditions such that the specific part may be sufficiently captured in the next image.

Generating a three-dimensional model of an anatomical structure may be found in the prior art, wherein reference is made to EP 1 611 863 and US 2006004284, both of which are hereby incorporated by reference in their entirety. The references disclose a method for generating a three-dimensional model of an anatomical structure with the aid of a surgical navigation system, wherein two fluoroscopy images are used. In this known method for generating a three-dimensional model of an anatomical structure, the position and orientation of the three-dimensional model relative to a tracking device is determined. The position of the tracking device is determined and tracked using a surgical navigation system. The method includes the following steps:

A tracking device that can be detected by a sensor, in particular a navigation system, can be attached to an anatomical structure.

The positions of landmarks on the anatomical structure may be identified using a pointing device (a contact or non-contact pointer that may include a tip and a tracking device and/or may include a laser).

A three-dimensional model of the anatomical structure and its spatial position may be calculated.

A C-arm, which can be detected and tracked by the navigation system, is moved to at least two positions. The two positions are suitable for recording x-ray images of the anatomical structure. The position of the C-arm, in particular the position of the imaging part of the C-arm relative to the anatomical structure, can be displayed by the navigation system, in order to guide a user.

An improved three-dimensional model of the anatomical structure and its spatial relation to a tracking device may be calculated.

The method in accordance with the invention can include individual steps or all of the steps of the aforesaid method. To determine given imaging conditions, landmarks of the anatomical structure (or the specific part) can be touched using a pointer to determine the position of the anatomical structure relative to the imaging apparatus using a sensor. The sensor may be included in a navigation system. A movable control unit for an x-ray source and an x-ray target may be found in U.S. Pat. No. 6,200,024B1, which is hereby also incorporated by reference in its entirety. The ability to control the movement of the imaging apparatus is included in an embodiment in accordance with the present invention. If a source and a target are required for imaging, then a specific spatial relation can be maintained between the source and the target when one of the two is moved in order to change the imaging conditions.

EP 1 056 572 B1, which is hereby also incorporated by reference in its entirety, discloses a general method for registering the position of a robot relative to a work piece, wherein the robot can support an imaging unit. An imaging unit that can be attached to and supported by a movable robotic device or arm is included in accordance with an embodiment of the present invention.

BRIEF DESCRIPTION OF THE DRAWINGS

The forgoing and other features of the invention are hereinafter discussed with reference to the drawings.

DETAILED DESCRIPTION

Figure 1:
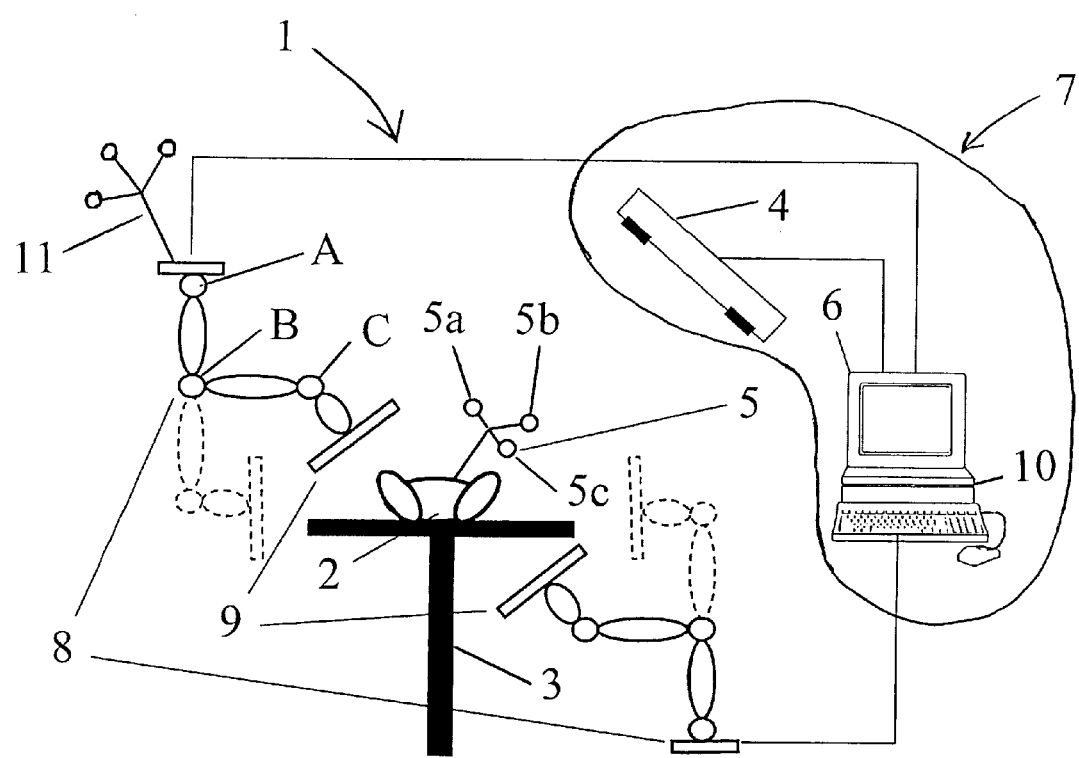
FIG. 1 schematically shows the design of an exemplary device in accordance with the invention.

The method in accordance with the invention can allow a specific part of an anatomical structure, or a three-dimensional model of the specific part, to be captured by an imaging apparatus. The three-dimensional model may be registered using the position of the three-dimensional model in a reference frame determined using a navigation system.

In addition to one or more of the steps of the method described above in connection with EP 1 611 863, the method in accordance with the invention includes one or more of the following steps Calculate optimum positions of an imaging apparatus (e.g. an x-ray machine in a C-arm), based on a rough three-dimensional model of the anatomical structure (or the specific part) and navigation data (captured using a sensor and/or a navigation system), wherein the navigation data may be particular data that has been captured using a tracking device and/or pointers that are attached or secured in relation to the anatomical structure.

The optimum position of the imaging device may be determined using different criteria for the spatial relation between the objects, the objects including the imaging apparatus and the specific part. Different imaging directions may be proposed for different parts of the anatomical structure to obtain the best possible three-dimensional models depending on the respective part of the anatomical structure. As disclosed above, the respective imaging directions may be stored in a database.

The imaging apparatus may be configured such that the position of an imaging unit of the imaging apparatus, which takes the actual image, can be adjusted. To this end, the imaging apparatus may include a controllable robot arm or a controllable and jointed mechanism that may allow the imaging unit to be moved to new positions and/or orientations relative to the specific part, to set new imaging conditions.

New positions for the imaging unit to assume are desired and can be calculated if the calculation of the three-dimensional model and/or the determination of the spatial position and orientation can not be completed to a specified degree of accuracy.

Positions and/or spatial relations between objects and/or the result of registration can be stored, whether or not the registration was successful. The device in accordance with the invention can include a database that can be used in future calculations for calculating optimum imaging conditions, such as the position and orientation of the imaging unit.

The imaging unit may be automatically positioned in accordance with the invention. This can save time as compared to manually positioning the imaging unit. Also, calculating the optimum imaging conditions in accordance with the invention can reduce the necessary number of recordings, or images. The positions of other apparatus may also be captured and/or stored. Capturing the positions of the other apparatus, particularly those pieces that can disrupt imaging, may be achieved using tracking devices that are attached or secured to the apparatus and tracked by a navigation system. If the positions of the apparatus are stored, the stored positions may be used later in the method or by the device in accordance with the invention to calculate whether one of the apparatus is disrupting imaging. In other words, the positions may be used to determine whether the apparatus is lying within a spatial range that is captured by the imaging unit. The imaging conditions may be calculated so that the imaging process is not disrupted by the apparatus, in particular any apparatus lying between the imaging unit and the specific part.

In one embodiment, the x-ray source and the x-ray target (i.e. an apparatus sensitive to x-ray radiation) may be mounted on separate movable and/or robotic arms. This mounting enables a more flexible selection of the imaging directions and thus of the imaging conditions, as compared to a conventional C-arm. With independent mounting and movement, many different imaging directions and a greater number of degrees-of-freedom in the movement of the actuating arms can be obtained.

The imaging apparatus and the data processing computer can be configured for direct data exchange. If the image or images captured and stored do not meet the minimum requirements of an image analyzing algorithm, alternative imaging conditions may be calculated and the arms of the imaging apparatus that can be actuated may be automatically controlled until the correct image content has been obtained. In other words, if an incorrect section of the anatomical structure was obtained by the first image, the imaging conditions may be changed such that the correct section is obtained by the next image.

The three-dimensional model already calculated may be used to calculate imaging conditions for the next image to optimize the three-dimensional model using another image. The three-dimensional model may be a rough model based on database information, the spatial location of which is based on rough pre-registration (for example, by using pointers and landmarks). Using the method in accordance with the invention, the three-dimensional model can be registered relative to the imaging apparatus and/or within a reference frame (for example, the navigation system).

The method and device in accordance with the invention can automatically position the imaging unit. This automation enables an operator to keep away from an imaging apparatus, such as an x-ray machine, to which exposure may be hazardous to the operator's health.

Automating the changes to the imaging conditions can also increase the chances of converging the calculation of a three-dimensional model.

By storing the imaging conditions, such as position data for the imaging unit from earlier imaging processes and from sequences of images, it is possible to gain experience in order to optimize the calculation of future imaging conditions.

FIG. 1 shows an exemplary device 1 in accordance with the invention that allows the method in accordance with the invention to be explained by way of example. The device 1 can generate a three-dimensional model of a specific part 2 of an anatomical structure positioned on a table 3. The device 1 can also determine the position and/or orientation of the specific part 2. This position and/or orientation information can be determined within a reference frame in which the specific part 2 lies or in which a sensor 4 of the device 1 lies. The position and/or orientation of the specific part 2 can be determined relative to a tracking device 5 (including marker spheres 5a, 5b, 5c), the position of which is detected and tracked by the sensor 4 and calculated by a data processing computer 6. The sensor 4 and the data processing computer 6 can together form a navigation system 7, which can be used to track surgical instruments equipped with similar tracking devices. The device 1 in accordance with the invention may or may not include the navigation system 7.

The device 1 in accordance with the invention may also include an imaging apparatus 8, which may include imaging units 9, the position of which can be changed using an arm with a plurality of joints A, B, and C. Examples of alternative positions for the imaging units 4 are indicated in FIG. 1 by dashed lines. The imaging apparatus 8 may provide two-dimensional images to the data processing computer 6. The anatomical structure and, to the extent possible, the specific part 2 are imaged. The imaging apparatus 8 may include a movable and/or robotic arm, as indicated schematically including a plurality of joints (A, B, C) that support and position the imaging unit 9 to set the imaging conditions. The position of the imaging unit 9, and the arm of the imaging apparatus 8, may be controlled by the data processing computer 6.

The imaging conditions, i.e., the position and/or orientation of the imaging unit 9, may be calculated by the data processing computer 6, to determine the imaging conditions for subsequent images, or a subsequent sequence of imaging conditions. The data processing computer 6 can also include an anatomical database 10 which may allow an imaged part to be identified and allow the imaging conditions to be determined. The sequence of imaging conditions may be optimized in this way to enable a three-dimensional model of the specific part 2 of the anatomical structure to be calculated using as few images as possible. In particular, the location of the three-dimensional model of the specific part 2 may be determined in a reference frame of the navigation system 7. A reference frame of the navigation system 7 can be defined relative to the tracking device 5. The tracking device 5 may be configured such that it can be detected by the sensor 4 and imaged by the imaging apparatus 8. The marker elements (marker spheres 5a, 5b, 5c) can be both optically detectable (e.g., actively emit or passively reflect infrared light), and be impermeable to x-ray radiation. Such markers are detectable to an imaging apparatus 8 such as an x-ray machine. With such markers, it is possible to capture the location of the tracking device 5 relative to the anatomical structure using the imaging apparatus 8. Since the location of the tracking device 5 may also be determined by the navigation system 7 in a defined reference frame (for example, the operating room), the location of the specific part 2 can be determined in the reference frame by the device 1 in accordance with the invention.

The position of the imaging units 9 can be known by controlling their position using the data processing computer 6. To verify and/or capture the position of the imaging units 9, a tracking device 11 can be attached to the imaging units 9. The tracking device 11 can be detected and tracked by the sensor 4 to determine the relative location between the imaging unit 9 and the tracking device 5. Information concerning the imaging conditions can also be improved in this way because the information is more exact if the relative location between the tracking device 11 and the specific part 2 is known. This information can then be used to determine the imaging conditions or can be incorporated into determining the imaging conditions using the database 10 and based on the imaged part.

Preferably, a three-dimensional model of a specific part 2 of an anatomical structure can be generated, and the position of the specific part 2 and its orientation relative to at least one tracking device 5 can be determined. The position of the tracking device 5 can be tracked by the surgical navigation system 7. The position of the imaging apparatus 8—more specifically, of the imaging unit 9—can be at least partly controlled by data processing computer 6, and/or by the navigation system 7. The positions of the imaging units 9 can be optimized in order to arrive at imaging conditions that are suitable for calculating a three-dimensional model of the specific part 2. The imaging unit 9 can be positioned and oriented relative to the tracking device 5.

Desired positions and/or orientations of the imaging unit 9 can be described by the spatial relation between objects, wherein the location of the objects can be detected and tracked by the sensor 4 or determined by the navigation system 7, and used as follows:

1. The spatial relation can be described by an angle between the imaging unit 9 and the longitudinal axis of the patient's body (not shown).
2. The spatial relation can be described by an angle between the imaging unit 9 and a plane of symmetry of the anatomical structure, for example a plane of symmetry of the pelvis (not shown).
3. The spatial relation can be described by a distance between the imaging unit 9 and the specific part 2 of the anatomical structure. With regard to the imaging properties of an imaging apparatus, this distance can be selected such that the specific part 2 assumes a particular size in the image.
4. The spatial relation can be described by a relative angle or relative position between the imaging unit 9 and the table 3.
5. The spatial relation can be specified by specifying a relative position of the imaging unit 9 relative to other apparatus (in the operating room), the position of which is detected and captured by the navigation system 7 or a sensor 4 or any other detection apparatus which can be integrated in the imaging unit 9.
6. The spatial relation between the imaging unit 9 and the specific part 2 can be described based on a maximum angle between imaging projections provided at a current position or a target position and the imaging projections resulting from a preceding image.

A method for automatically positioning an imaging unit 9 or the imaging apparatus 8 may include the following steps:

A first set of at least two positions of the imaging unit 9 can be determined, based at least in part on initial information concerning the anatomical structure and on the position and orientation of the anatomical structure as captured using a navigation system 7.

The imaging unit 9 can be moved using a control unit that controls the movement of a movable support structure (joints) of the imaging apparatus 8. The movement may be controlled based on data from the navigation system 7 to move the imaging unit 9 to the positions determined to be suitable. And the imaging unit 9 may be controlled to capture an image at each position.

At least two images may be used as a starting point for calculating a three-dimensional model of the specific part 2 of the anatomical structure.

The three-dimensional model is calculated, and the position and orientation of the three-dimensional model relative to a tracking device 5 attached to the specific part 2 and/or to the anatomical structure may be calculated.

A registered three-dimensional model of the specific part 2 may be used for surgical navigation.

Figure 2:
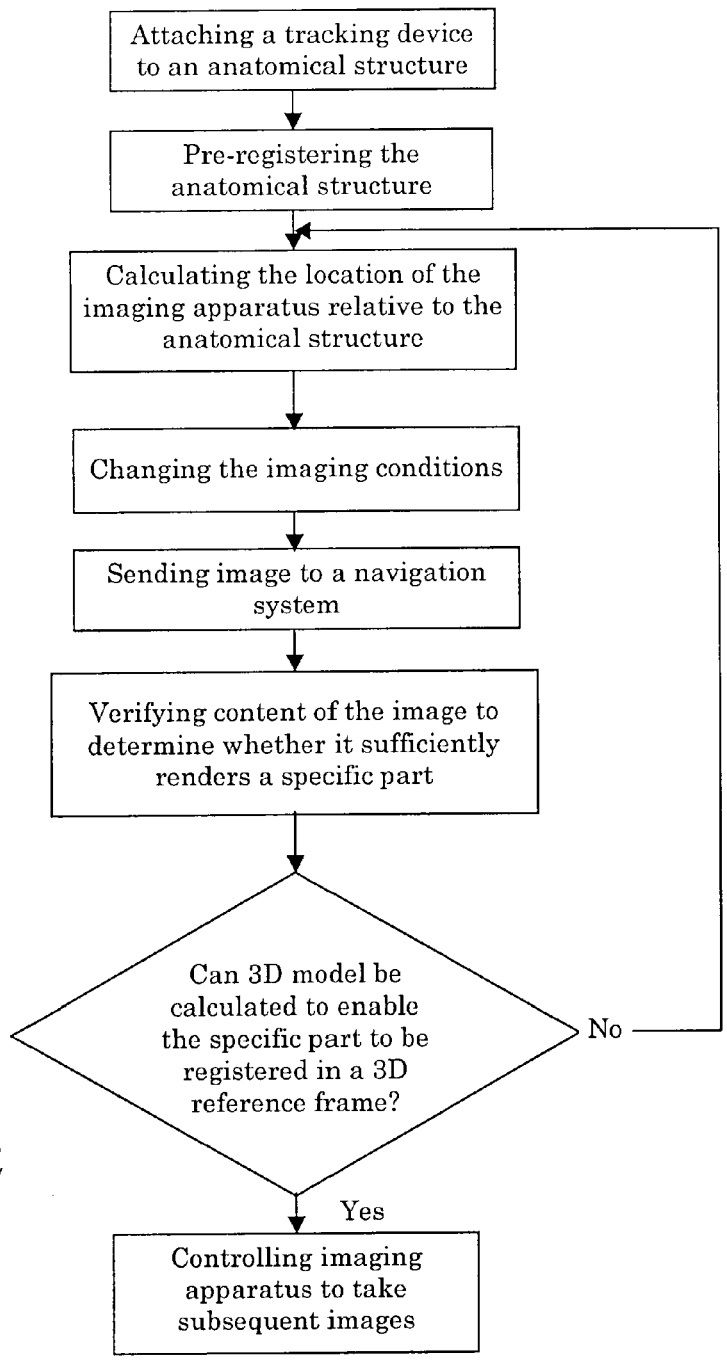
FIG. 2 shows the workflow of an exemplary method in accordance with the invention.

FIG. 2 schematically shows an exemplary workflow for determining a three-dimensional model. First, a tracking device may be attached to the anatomical structure or patient. Pre-registration may then be performed (i.e., the location and orientation of the anatomical structure, in particular the specific part, may be spatially determined). The relative location and/or orientation of the imaging unit relative to the anatomical structure, in particular the specific part, may then be calculated. The imaging apparatus, in particular the imaging unit, may then be actuated or re-actuated, to capture an image using a particular projection (i.e., under particular imaging conditions). The captured image may then be sent to the navigation system, where the image content is verified, in particular as to whether it meets predetermined conditions (e.g., whether it sufficiently renders the specific part). The next step may be to verify whether the images captured allow a three-dimensional model to be calculated and, in particular whether the specific part to be three-dimensionally registered in a reference frame of the navigation system can be calculated. If this is not the case, the above steps—beginning with calculating the location of the imaging apparatus relative to the anatomical structure—may be repeated, until a three-dimensional model can be calculated and/or three-dimensional model registration information can be determined. If this condition is met, then said calculation may be performed. The imaging apparatus can be controlled in order to take subsequent images under different imaging conditions.

Figure 3:
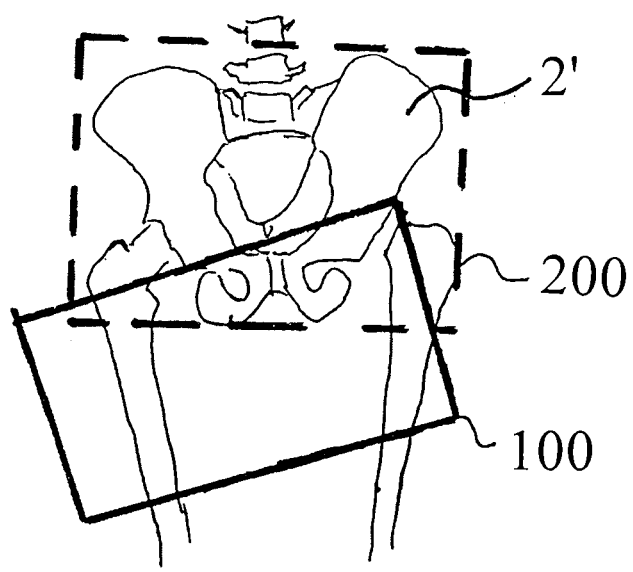
FIG. 3 schematically shows the principle of changing the imaging conditions.

FIG. 3 shows parts of an anatomical structure captured by a first image 100 and a second image 200. The specific part to be captured by the image(s) is the pelvis 2', which is captured by the second image 200. The first image 100 only captures a part of the pelvis 2'. The part imaged by the first image 100, which includes parts of the femur, may be compared with a database in order to identify which part of the anatomical structure has been captured by the first image 100, and determine how this structure lies relative to the specific part. On this basis, the imaging conditions may be changed (e.g., the position of an imaging unit 9 is moved) such that the specific part—in this example, the pelvis 2'—is captured by a second image 200. Thus, on the basis of an evaluation of the anatomical structure captured by the first image 100, the imaging conditions can be changed such that the specific part is desirably captured by a second image 200.

Although the invention has been shown and described with respect to a certain preferred embodiment or embodiments, it is obvious that equivalent alterations and modifications will occur to others skilled in the art upon the reading and understanding of this specification and the annexed Figures. In particular regard to the various functions performed by the above described elements (components, assemblies, devices, software, computer programs, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for capturing a specific part of an anatomical structure using a series of images, comprising:
   producing an image of an imaged part of the anatomical structure using a set of imaging conditions; and
   determining at least one of the imaging conditions by comparing the produced image to information stored in a database, said database comprising information concerning the anatomical structure.

2. The method according to claim 1, further comprising determining a change in the set of imaging conditions that enable the specific part of the anatomical structure to be captured in a subsequent image, said change in the set of imaging conditions based on i) the determined at least one imaging condition and ii) the information stored in the database concerning the anatomical structure.

3. The method according to claim 2, comprising producing the subsequent image of the imaged part using a new set of imaging conditions that include the determined change.

4. The method according to claim 2, wherein a relative location of the specific part relative to an imaging range is determined with the aid of the database, and the change to the imaging conditions is determined based on the relative location.

5. The method according to claim 2, further comprising providing type information to determine a type of imaging used to obtain the image, and wherein the change to the imaging conditions is further determined based on the type information.

6. The method according to claim 4, further comprising repeatedly changing the imaging conditions until it is established that the imaged part corresponds to the specific part, within the bounds of a predetermined tolerance.

7. The method according to claim 1, further comprising identifying the imaged part based on the information stored in the database and on an assumption that the imaged part is lying in the vicinity of the specific part.

8. The method according to claim 3, further comprising:
   obtaining a series of two-dimensional images; and
   producing a three-dimensional model of the specific part from the series of two-dimensional images.

9. The method according to claim 8, wherein the database includes different suitable imaging conditions for different stored parts of the anatomical structure and wherein the different stored parts are suitable for producing a three-dimensional model on the basis of the two-dimensional images produced under the suitable imaging conditions.

10. The method according to claim 9, further comprising:
    determining, based on the information stored in the database, which of the stored parts match the specific part; and
    determine, based on the information stored in the database, the suitable imaging conditions for a first and/or subsequent image based on the stored part which has been determined to match the specific part and further based on the imaging conditions associated with the stored part.

11. The method according to claim 3, further comprising:
    obtaining a series of two-dimensional images; and
    using an algorithm to derive from the series of images a three-dimensional model of the specific part, wherein if the algorithm does not converge or the three-dimensional model does not meet a predetermined accuracy, a new image is obtained under a new imaging condition that is different from the imaging conditions used to obtain the previous series of images.

12. The method according to claim 11, wherein obtaining a new image includes obtaining a series of new images.

13. The method according to claim 11, further comprising storing i) the imaging conditions used to produce the three-dimensional model of the specific part, and ii) the number of images used to derive the three-dimensional model to the predetermined accuracy.

14. The method according to claim 13, further comprising referring to the stored imaging conditions when selecting a subsequent imaging condition.

15. The method according to claim 12, further comprising varying the imaging conditions from image series to image series to optimize, in accordance with a learning process, the number of images, the imaging conditions associated with the respective images, and/or the accuracy of the three-dimensional model for each of a number of stored parts of the anatomical structure.

16. The method according to claim 1, further comprising attaching a tracking device the anatomical structure, the patient, and/or to a mechanical orientation aid with respect to which the patient is to assume a particular location, wherein the tracking device is detected by a sensor and/or an imaging apparatus that obtains the images, to determine a location and/or orientation of the imaging apparatus relative to the patient and/or the specific part, and to determine an imaging condition based on the relative location and/or orientation.

17. The method according to claim 1, further comprising attaching a tracking device to an imaging apparatus, wherein the tracking device is detected by a sensor to determine a location and/or orientation of the imaging apparatus relative to the patient and/or the specific part, and to determine an imaging condition based on the relative location and/or orientation.

18. A computer program embodied on a non-transitory computer readable medium for capturing a specific part of an anatomical structure using a series of images, comprising:
   code that produces an image of an imaged part of the anatomical structure using a set of imaging conditions; and
   code that determines at least one of the imaging conditions by comparing the produced image to information stored in a database, said database comprising information concerning the anatomical structure.

19. A device for capturing a specific part of an anatomical structure using a series of two-dimensional images, comprising:
   an imaging apparatus operable to obtain an image of a part of an anatomical structure;
   a database in which information is stored concerning the anatomical structure; and
   a data processing computer configured to
      i) consult or query the database to obtain information concerning the anatomical structure
      ii) compare an image of the part of the anatomical structure obtained by the imaging apparatus with the information stored in the database, and
      iii) determine at least one of the imaging conditions used in obtaining the image of the part of the anatomical structure.

20. The device according to claim 19 further comprising:
   an input device for receiving information for identifying the specific part in the database,
   wherein the data processing computer is configured to determine a set of changed imaging conditions intended to capture the specific part in at least one subsequent image, said determination based on the least one of the imaging conditions, and further based on the received information for identifying the specific part in the database.

21. The device according to claim 19 further comprising:
   a robotic motion device, in communication with the data processing computer, that is adapted to position the imaging apparatus to obtain images of the part of the anatomical structure using different imaging conditions.

22. A method for capturing a specific part of an anatomical structure using a series of images, comprising:
   producing an image of an imaged part of the anatomical structure using a set of imaging conditions;
   comparing the produced image to information stored in a database, said database comprising information concerning the anatomical structure; and
   revising at least one of the imaging conditions based on the comparison.

* * * * *